United States Patent [19]

Wedenig et al.

[11] Patent Number: 4,789,334

[45] Date of Patent: Dec. 6, 1988

[54] DENTAL MOLD FOR UPPER AND LOWER JAW

[76] Inventors: Wolfgang Wedenig; Wilfried Resch, both of Bahnjofstr. 16, A-9300 St. Veit, Austria

[21] Appl. No.: 133,557

[22] Filed: Dec. 16, 1987

[30] Foreign Application Priority Data

Dec. 16, 1986 [AT] Austria ................................. 3346/86

[51] Int. Cl.⁴ ............................................... A61C 9/00
[52] U.S. Cl. ......................................... 433/37; 433/42
[58] Field of Search ...................... 433/37, 41, 45, 42

[56] References Cited

U.S. PATENT DOCUMENTS 1,672,523  6/1928  Gregg ................................... 433/42

FOREIGN PATENT DOCUMENTS 42483  7/1933  France .................................. 433/41

*Primary Examiner*—Robert Peshock
*Attorney, Agent, or Firm*—Herbert Dubno

[57] ABSTRACT

A mold for taking impressions of upper and lower jaws has a main part including a U-shaped generally flat base plate having a rearwardly concave and open U-shaped inner periphery and a forwardly convex U-shaped outer periphery, a U-shaped rim projecting transversely of the plate from the outer periphery thereof, and a handle projecting forward from the outer periphery and formed with a rearwardly open passage. This main part can be used with either an upper-jaw or lower-jaw insert. The upper-jaw insert has a U-shaped upper-jaw wall generally complementarily fittable in an engaged position with the inner periphery of the base plate to form therewith a transversely open U-shaped recess adapted to receive molding compound, a palate plate bridging the U-shaped upper-jaw wall, and a stem projecting forward from the upper-jaw wall and engageable in the passage when the upper-jaw wall and rim define the recess. The lower-jaw insert has a U-shaped lower-jaw wall generally identical to the upper-jaw wall but forming a rearwardly open tongue-accommodating cutout and a stem projecting forward from the lower-jaw wall and engageable in the passage when the lower-jaw wall and rim define the recess. The main part is provided with a system for arresting either of the stems in the passage in any of several relative positions of the inserts and main part.

6 Claims, 2 Drawing Sheets

DENTAL MOLD FOR UPPER AND LOWER JAW

FIELD OF THE INVENTION

The present invention relates to a dental mold. More particularly this invention concerns such a mold used to take the impression of the upper or lower human jaw and any teeth therein.

BACKGROUND OF THE INVENTION

Austrian Pat. No. 53,763 describes a dental mold formed of a main part and an insert. The main part forms most of the U-shaped recess that holds the material that receives the impression and the insert has a portion shaped like the palate and which can be fitted into a cutout in the main part. Such a mold, typically referred to as a spoon, is extremely uncomfortable for the patient whose tongue is given no room when it is used. In addition such a mold is usable only to take an upper-mandible impression.

The impression material, which typically is a gypsum-type material that becomes extremely rigid, hardens in the patient's mouth and is left on the jaw while the mold is separated from it. Then the impression must be broken apart to get it out. Once removed, the parts are reassembled into the desired negative mold and the bridge, plate, or other dental device can be made using it.

Modern-day elastic impression materials are normally held in a one-piece spoon and are removed with this spoon from the patient's mouth once the material has cured enough to hold shape. The spoon is left on the cured negative impression which is filled with the hard plaster or the like used to make the positive impression. Separation of this positive impression from the material in the mold is problematic in that this positive impression frequently breaks during separation.

OBJECTS OF THE INVENTION

It is therefore an object of the present invention to provide an improved dental mold.

Another object is the provision of such a dental mold which overcomes the above-given disadvantages, that is which can be used on both upper and lower jaws and which can be separated from the impression without damage to it or the impression.

SUMMARY OF THE INVENTION

A mold for taking impressions of upper and lower jaws according to this invention has a main part including a U-shaped generally flat base plate having a rearwardly concave and open U-shaped inner periphery and a forwardly convex U-shaped outer periphery, a U-shaped rim projecting transversely of the plate from the outer periphery thereof, and a handle projecting forward from the outer periphery and formed with a rearwardly open passage. This main part can be used with either an upper-jaw or lower-jaw insert. The upper-jaw insert has a U-shaped upper-jaw wall generally complementarily fittable in an engaged position with the inner periphery of the base plate to form therewith a transversely open U-shaped recess adapted to receive molding compound, a palate plate bridging the U-shaped upper-jaw wall, and a stem projecting forward from the upper-jaw wall and engageable in the passage when the upper-jaw wall and rim define the recess. The lower-jaw insert has a U-shaped lower-jaw wall generally identical to the upper-jaw wall but forming a rearwardly open tongue-accommodating cutout and a stem projecting forward from the lower-jaw wall and engageable in the passage when the lower-jaw wall and rim define the recess. The main part is provided with a system for arresting either of the stems in the passage in any of several relative positions of the inserts and main part.

According to this invention each of the stems has a narrow edge provided with formations interengageable with the locking device. A succession of notches or the like can constitute these formations. In addition each of the stems projects from a forward end of the handle in a position with the respective insert fully engaged with the main part. This makes it possible to open up the mold after the impression material has hardened simply by striking the protruding end of the insert stem to push it away from the main part and allow the impression material to be lifted without fracturing out of the mold recess.

According to another feature of this invention each of the inserts has a pair of wall parts forming in the engaged position extensions of ends of the rim of the main part. Furthermore the rim has an overreaching free edge that keeps the impression material partly captured, but that nonetheless does not interfere with demolding the impression once the insert has been pushed back out of the main part.

DESCRIPTION OF THE DRAWING

The above and other objects, features, and advantages will become more apparent from the following, reference being made to the accompanying drawing in which.

SPECIFIC DESCRIPTION

Figure 1:
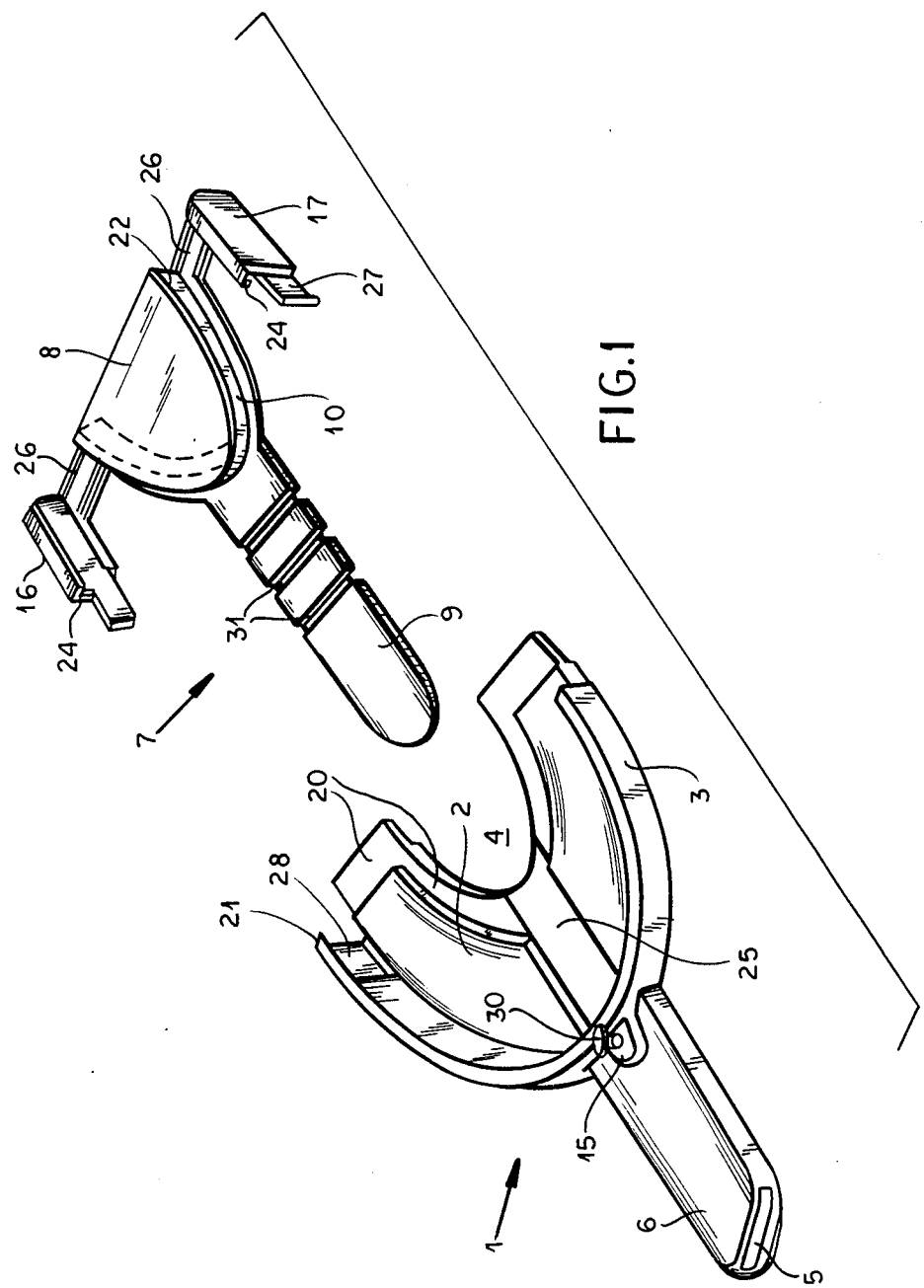
FIG. 1 is an exploded view of the mold according to this invention for taking the impression of an upper mandible and any teeth therein.

As seen in FIG. 1 a mold according to this invention has a main part or spoon 1 basically constituted as a flat U-shaped plate 2 provided along most of its outer periphery with an upstanding rim or wall 3 and having an inner periphery defining a generally semicircular or parabolic cutout 4. In addition the part 1 has a handle 6 projecting forward from the center of its outer periphery and parallel to the plane of the upper surface of the base plate 2. This handle 6 is formed with a longitudinally throughgoing rectangular-section passage 5 continued in the plate 2 as an upwardly open groove 25.

For taking an impression of an upper jaw this base part 1 is used with an insert 7 having a flat plate 8 shaped generally to lie on the upper palate and having a downwardly directed U-shaped rim or wall 10 from whose forward end projects a stem 9 of a section complementary to but slightly smaller than the passage 5 and groove 25. When this stem 9 is slid forward along the groove 25 and through the passage 5 the rim 10 and the rim 3 bound the sides of an upwardly open U-shaped recess that is filled with impression compound.

The upper edge of the rim 3 is bent inward at 21 and the upper edge of the wall 10 is bent outward so that this mass will be captured in the recess. In addition the stem 9, which projects from the forward end of the passage 5 when the insert 7 is fully engaged in the base 1, can be locked in the passage 5 by a screw 30 inserted into a hole 15 to arrest the two parts 1 and 7 relative to each other. This screw 30 can catch in grooves 31 or other formations on the stem 9 to establish relative indexing positions, that is for locking the two parts 1 and 7 relative to each other. The forward projection of the stem 9 from the handle 6 makes separating the two parts 1 and 7 easy once the molding material is hard in that a backward blow to the projecting end of the stem 9 will surely push the insert 7 back away from the part 1.

In addition the rim 10 is formed at its outer ends with outwardly projecting arms 26 from whose ends extend forward wall portions 16 and 17 of the same cross section as the rim 3 and having bent-over upper edges 24 like the edges 21. Forwardly projecting tongues 27 from these wall portions 16 and 17 can fit within complementary seats 28 of the rim 3, and similarly the plate 2 is extended at its ends and inner periphery at 20 to engage under and lock with the insert 7. Thus the assembled upper-mandible mold is extremely durable, yet it can be taken apart easily to free the negative impression without any damage to this impression.

Figure 2:
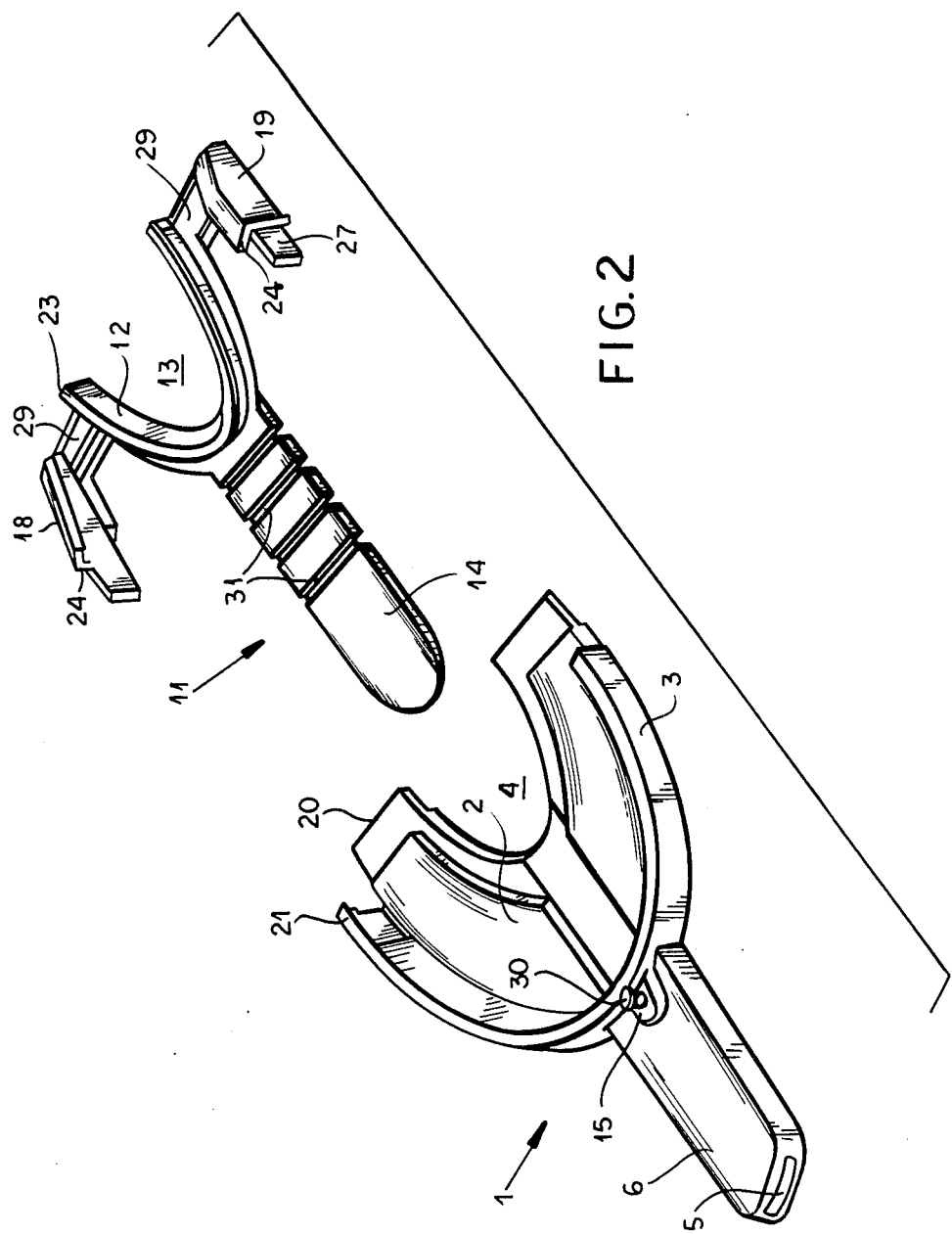
FIG. 2 is a similar view of the mold for the lower mandible and its teeth.

To take an impression from a lower mandible and its teeth, the insert 11 of FIG. 2 is used. It has a U-shaped ridge 12 defining a cutout 13 like the cutout 4 and having a forwardly projecting stem 14 substantially identical to the stem 9 of FIG. 1. In addition the rear ends of the ridge 12 have lateral extensions 29 like the extensions 26 and formed with forwardly projecting wall portions 28 and 19 identical to the portions 16 and 17. This insert 11 works identically to the insert 7, but the open cutout 13 accommodates the patient's tongue while taking the impression.

With both setups the finished impression, even if of very hard material, can be freed from the mold without chipping or damaging it at all. The mold parts are not deformed at all to free the impression, so that they can be expected to have a very long service life. What is more, it is possible to set the insert 7 or 11 somewhat out from the main part to accommodate a particularly large jaw, in effect making the size of the mold adjustable and thereby reducing the range of such molds the dentist need keep on hand.

We claim:

1. A mold for taking impressions of a upper or a lower jaws, the mold comprising:
   a main part including
      a U-shaped generally flat base plate having a rearwardly concave and open U-shaped inner periphery and a forwardly convex U-shaped outer periphery,
      a U-shaped rim projecting transversely of the plate from the outer periphery thereof, and
      a handle projecting forward from the outer periphery and formed with a rearwardly open passage;
   an upper-jaw insert including
      a U-shaped upper-jaw wall generally complementarily fittable in an engaged position with the inner periphery of the base plate to form therewith a transversely open U-shaped recess adapted to receive molding compound,
      a palate plate bridging the U-shaped upper-jaw wall, and
      a stem projecting forward from the upper-jaw wall and engageable in the passage when the upper-jaw wall and rim define the recess;
   a lower-jaw insert including
      a U-shaped lower-jaw wall generally complementarily fittable in an engaged position with the inner periphery of the base plate to form therewith a transversely open U-shaped recess adapted to receive molding compound, the lower-jaw wall forming a rearwardly open tongue-accommodating cutout, and
      a stem projecting forward from the lower-jaw wall and engageable in the passage when the lower-jaw wall and rim define the recess; and
   means for arresting either of the stems in the passage in any of several relative positions of the inserts and main part.

2. The mold defined in claim 1 wherein each of the stems has a narrow edge provided with formations interengageable with the means.

3. The mold defined in claim 1 wherein each of the stems projects from a forward end of the handle in a position with the respective insert fully engaged with the main part.

4. The mold defined in claim 1 wherein each of the inserts has a pair of wall parts forming in the engaged position extensions of ends of the rim of the main part.

5. The mold defined in claim 1 wherein the rim has an overreaching free edge.

6. The mold defined in claim 1 wherein the inserts can be secured by the arresting means in any of a plurality of positions offset longitudinally of the passage.

* * * * *